United States Patent
Lackey et al.

(10) Patent No.: US 9,732,113 B2
(45) Date of Patent: Aug. 15, 2017

(54) DENDRIMERIC DYE-CONTAINING OLIGONUCLEOTIDE PROBES AND METHODS OF PREPARATION AND USES THEREOF

(71) Applicant: Agilent Technologies, Inc., Loveland, CO (US)

(72) Inventors: Jeremy Lackey, San Jose, CA (US); Siyuan Chen, Santa Clara, CA (US); Maithreyan Srinivasan, Santa Clara, CA (US)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 516 days.

(21) Appl. No.: 14/153,062

(22) Filed: Jan. 12, 2014

(65) Prior Publication Data

US 2014/0272934 A1    Sep. 18, 2014

Related U.S. Application Data

(60) Provisional application No. 61/778,788, filed on Mar. 13, 2013.

(51) Int. Cl.
*C07H 19/04* (2006.01)
*C07H 21/00* (2006.01)
*C12Q 1/68* (2006.01)
*C40B 40/06* (2006.01)

(52) U.S. Cl.
CPC ............. *C07H 21/00* (2013.01); *C12Q 1/682* (2013.01); *C12Q 1/6841* (2013.01)

(58) Field of Classification Search
CPC ...................................................... C07H 21/00
USPC ............................ 506/16; 536/26.6; 435/6.1
See application file for complete search history.

(56) References Cited

U.S. PATENT DOCUMENTS 8,889,635 B2 * 11/2014 Baker, Jr. ......... A61K 47/48207
  514/22
2004/0023248 A1 * 2/2004 O'Malley .............. C12Q 1/682
  506/9

* cited by examiner

*Primary Examiner* — Jezia Riley

(57) ABSTRACT

The invention provides novel oligonucleotide probes that have dendrimeric dyes useful for detecting and analyzing biological samples, and compositions and methods thereof. The dendrimeric dye-containing oligonucleotide probes are useful for high sensitivity fluorescence in situ hybridization (FISH) of nucleic acids such as DNA and RNA.

8 Claims, 1 Drawing Sheet

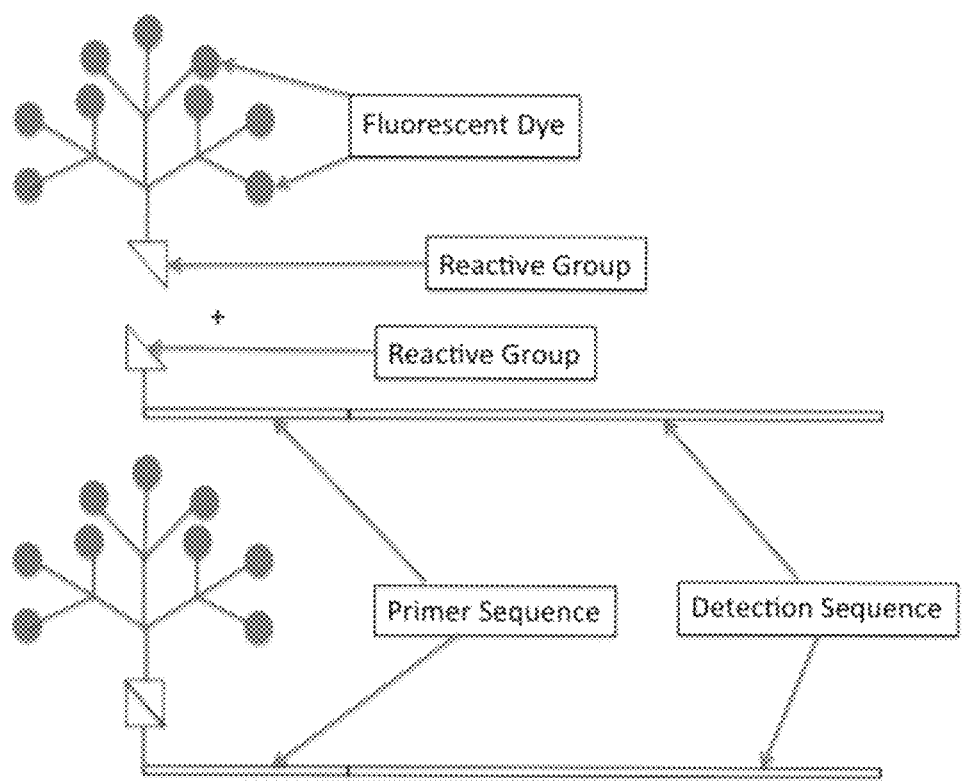

US 9,732,113 B2

DENDRIMERIC DYE-CONTAINING OLIGONUCLEOTIDE PROBES AND METHODS OF PREPARATION AND USES THEREOF

PRIORITY CLAIMS AND RELATED APPLICATIONS

This application claims the benefit of U.S. Provisional Application No. 61/778,788, filed Mar. 13, 2013, the entire content of which is incorporated herein by reference in its entirety.

FIELD OF THE INVENTION

The invention generally relates to probes for biodetection and analyses of biological samples. More particularly, the invention relates to oligonucleotide probes that feature dendrimeric dyes useful for detecting and analyzing biological samples, and compositions and methods thereof.

BACKGROUND OF THE INVENTION

Fluorescence in situ hybridization (FISH) has evolved into a powerful tool for biological research and medicine since the 1980s. FISH is a cytogenetic technique used to detect and localize the presence or absence of specific DNA sequences on chromosomes. (Langer-Safer, et al. 1982 *Proc. Natl. Acad. Sci. U.S.A.* 79 (14): 4381-5.) Fluorescent probes and fluorescence microscopy are used in conjunction to identify specific features in DNA or detect and localize specific RNA targets (mRNA, lncRNA and miRNA) in cells, circulating tumor cells and tissue samples. (Amann, et al. 2008 *Nature Reviews Microbiology* 6: 339-348.) FISH is an important technique in assisting diagnosis and prognosis of a disease, such as cancer.

Fluorescent probes have become powerful tools for analyzing genes, tissues and cells. (Waggoner 1986 *Applications of Fluorescent in the Biomedical Sciences*, Eds. Taylor et al., New York: Alan R. Liss, Inc. pp. 3-28; Mason, editor 1993 *Fluorescent and Luminescent Probes for Biological Activity, Biological Techniques Series*, edited by Sattelle, Academic Press Limited, London.) Among others, commonly labeled biomolecules include nucleotides, oligonucleotides, nucleic acids, amino acids, peptides and polypeptides, proteins, carbohydrates and lipids. (Singer & Ward, 1982 *Proc. Natl. Acad. Sci. U.S.A.* 79:7331-7335; Singer et al. 1986 *BioTechniques* 4:230-250; Pitta et al. 1990 *Strategies* 3: 33; Southern, 1975 *J. Mol. Biol.* 98: 503-517; Alwine et al. 1977 *Proc. Natl. Acad. Sci. U.S.A.* 74: 5350-5354; Callow et al. 2000 *Grenome Res.* 10: 2027-2029.)

Previous fluorophore labeling methods used NTP (nucleoside triphosphate) dyes for labeling. (See, e.g., WO 2000/06773). Another fluorescent labeling technique used platinum compounds for nucleic acid labeling (See, e.g., EP1373572B1). The platinum-based labeling compounds attach to the target biomolecules via coordination of the platinum (II) metal center with nitrogen or sulfur atoms on the target biomolecule. The disadvantages of these strategies include that only a limited number of dyes can be introduced into the probes, thus limiting "brightness" of the probes. In addition, the NTP dyes can result in low yield due to poor incorporation of the highly-modified triphosphates, and the platinum-based compounds can cause degradation of the probes. Moreover, both strategies result in nucleobase modifications throughout the strand, including base pair regions that can negatively affect hybridization.

Thus, there remains an unmet need for novel fluorescent probes and fluorophore labeling methodologies that address the shortcomings of existing fluorescent probes and methods.

SUMMARY OF THE INVENTION

The invention is based in part on the unexpected discovery of novel oligonucleotide probes conjugated with dendrimeric dyes that are useful for detecting and analyzing biological samples.

These unique probes offer a number of advantages while overcoming the deficiencies of existing fluorescent probes. First, there is no limit to the amount of fluorescent dyes that can be incorporated in the probes. Second, it is know that dendrimeric dyes are brighter than their individual counterparts leading to a more sensitive probe. (See, e.g., US2012256102A1) Third, the use of click chemistry generally leads to quantitative or near quantitative labeling. Furthermore, since the dye-containing moiety will be at the 5'- of the FISH probe, the fluorescent moieties do not affect hybridization of the probe with the target species such as genomic DNA or RNA.

In one aspect, the invention generally relates to an oligonucleotide probe. The oligonucleotide probe includes a nucleic acid sequence capable of hybridization with a target nucleic acid of interest; and a primer covalently attached to the oligonucleotide, wherein the primer is covalently attached to a dendrimeric group comprising two or more fluorescent moieties.

In another aspect, the invention generally relates to a method for generating oligonucleotide probes. The method includes: generating a library of oligonucleotides; providing a plurality of primers each comprising an alkyne moiety; forming a library of amplicons wherein each amplicon comprises a member of the library of oligonucleotides and a primer from the plurality of primers; providing a dendrimeric group comprising two or more fluorescent moieties and comprises an azide moiety; and reacting the amplicons with the dendrimeric group by reacting the alkyne moiety with the azide moiety thereby generating a library of oligonucleotide probes.

In yet another aspect, the invention generally relates to a method for detecting or analyzing a target nucleic acid of interest. The method includes: providing an oligonucleotide probe comprising a nucleic acid sequence capable of hybridization with a target nucleic acid of interest and a primer covalently attached a first reactive moiety; contacting the oligonucleotide probe with a sample to be analyzed for the presence of the target nucleic acid of interest under a condition such that, if the target nucleic acid of interest is present, a hybridization complex is formed between the oligonucleotide probe and the target nucleic acid of interest; and reacting the contacted sample with a dedrimeric imaging agent comprising two or more fluorescent moieties and a second reactive moiety, whereby the second reactive moiety reacts with the first reactive moiety to form a covalent bond; and imaging the two or more fluorescent moieties to detect or analyze the presence of the target nucleic acid of interest.

BRIEF DESCRIPTION OF THE DRAWINGS

The FIGURE shows a schematic illustration of an embodiment of the oligonucleotide probe according to the invention.

DEFINITIONS

Unless defined otherwise, all technical and scientific terms used herein have the same meaning as commonly understood by one of ordinary skill in the art to which this invention belongs. Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, 2.sup.nd Edition (Cold Spring Harbor Laboratory, 1989); and the like. Still, certain terms are defined below for the sake of clarity and ease of reference.

The term "biomolecule" may refer to a compound found in nature, a derivative of a compound found in nature, a synthetically modified analog of a compound found in nature, a genetically engineered analog of a compound found in nature, a genetically engineered modified analog of a compound found in nature. For example, biomolecules may be and/or include proteins; antibodies; antibody-fragments; haptens; glycoproteins; cell-membrane proteins; enzymes, such as alkaline phosphatase, .beta.-galactosidase, horseradish peroxidase, or urease; peptides; peptide nucleic acids (PNAs); locked nucleic acids (LNAs); genetically engineered peptides; genetically engineered proteins; genetically engineered antibodies; genetically engineered antibody-fragments; oligonucleotides; RNA; DNA; saccharide-containing molecules; monosaccharides; disaccharides; trisaccharides; oligosaccharides; polysaccharides, such as dextran; small molecules, including drug-like molecules; drugs; antigens, such as tumor antigens; pathogens; toxins; polymers, including biopolymers and/or dendrimers; nuclear receptors; nuclear receptor substrates and/or ligands; cytokines; epitopes, including peptide epitopes, antigen epitopes, and/or pathogen epitopes; enzyme substrates; and/or combinations or derivatives thereof.

The term "sample", as used herein, refers to a material or mixture of materials, typically, although not necessarily, in liquid form, containing one or more analytes of interest.

The term "nucleic acid sample", as used herein, refers to a sample that includes nucleic acid. A sample may include a single nucleic acid species or any number of nucleic acid species. Certain samples include at least 10, at least 100, at least 1,000, or more (e.g., at least 100,000 or at least 1,000,000 different species) of different nucleic acid fragments or different sequences. A sample may be a biological sample from any source, e.g., a sample of cerebro-spinal fluid, lymph, blood, blood derivatives (e.g., sera), liquidized tissue, urine, fecal material, swab or nasal wash from a human, cell culture, or a foodstuff.

The term "genomic sample", as used herein, refers to a material or mixture of materials, including genetic material from an organism.

The term "genomic DNA", as used herein, refers to deoxyribonucleic acids that are obtained from an organism.

The terms "genomic sample" and "genomic DNA", as used herein, encompass genetic material that may have undergone amplification, purification, or fragmentation.

The term "label", as used herein, refers to any detectable label, including a radioactive label and a non-radioactive label. Non-radioactive labels include optically detectable labels, including fluorescent labels and fluorescent barcodes, as well as mass tagged labels. Labels include directly detectable and indirectly detectable non-radioactive labels such as fluorescent labels and mass tags.

The term "fluorescent label", as used herein, refers to any label detectable via fluorescent emission of the label, for example, via fluorescent spectroscopy. A biomolecule such as a nucleic acid can be directly or indirectly labeled. A nucleic acid that is directly labeled is linked to the label covalently or non-covalently.

The term "nucleotide", as used herein, refers to a sub-unit of a nucleic acid and has a phosphate group, a 5-carbon sugar and a nitrogen-containing base, as well as functional analogs (whether synthetic or naturally occurring) of such sub-units which, in the polymer form (as a polynucleotide), can hybridize with naturally occurring polynucleotides in a sequence specific manner analogous to that of two naturally occurring polynucleotides. Nucleotide sub-units of deoxyribonucleic acids are deoxyribonucleotides, and nucleotide sub-units of ribonucleic acids are ribonucleotides.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Generally, as used herein, the terms "oligonucleotide" and "polynucleotide" are used interchangeably. Further, generally, the term "nucleic acid" or "nucleic acid molecule" also encompasses oligonucleotides and polynucleotides.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1,000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleotides, e.g., can participate in Watson-Crick base pairing interactions. Naturally-occurring nucleotides include guanine, cytosine, adenine and thymine (G, C, A and T, respectively).

The term "oligonucleotide" as used herein denotes a single stranded multimer of nucleotide of from about 2 to 500 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. Oligonucleotides may be 10 to 20, 21 to 30, 31 to 40, 41 to 50, 51-60, 61 to 70, 71 to 80, 80 to 100, 100 to 150, 150 to 200 or greater than 200 nucleotides in length, for example.

The terms "ribonucleic acid" and "RNA", as used herein, refer to a nucleic acid composed of nucleotides ribonucleotides.

The terms "deoxyribonucleic acid" and "DNA", as used herein, refers to a nucleic acid composed of nucleotides deoxyribonucleotides.

The terms "hybridize" or "hybridization", as used herein, refer to the binding or duplexing of a nucleic acid molecule to a particular nucleotide sequence under suitable conditions, e.g., under stringent conditions. The term "stringent conditions" (or "stringent hybridization conditions") as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent conditions are the summation or combination (totality) of both hybridization and wash conditions.

Stringent conditions (e.g., as in array, Southern or Northern blotting or hybridizations) may be sequence dependent, and are often different under different experimental parameters. Stringent conditions that can be used to hybridize nucleic acids include, for instance, hybridization in a buffer comprising 50% formamide, 5×SSC (salt, sodium citrate), and 1% SDS at 42° C., or hybridization in a buffer comprising 5×SSC and 1% SDS at 65° C., both with a wash of 0.2×SSC and 0.1% SDS at 65° C. Other examples of stringent conditions include a hybridization in a buffer of 40% formamide, 1 M NaCl, and 1% SDS at 37° C., and a wash in 1×SSC at 45° C. In another example, hybridization to filter-bound DNA in 0.5 M NaHPO.sub.4, 7% sodium dodecyl sulfate (SDS), 1 mM EDTA at 65° C., and washing in 0.1×SSC/0.1% SDS at 68° C. can be employed. Yet additional examples of stringent conditions include hybridization at 60° C. or higher and 3×SSC (450 mM sodium chloride/45 mM sodium citrate) or incubation at 42° C. in a solution containing 30% formamide, 1 M NaCl, 0.5% sodium lauryl sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions that determine whether a nucleic acid is specifically hybridized to another nucleic acid (for example, when a nucleic acid has hybridized to a nucleic acid probe). Wash conditions used to identify nucleic acids may include, e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate. The terms "high stringency conditions" or "highly stringent hybridization conditions," as previously described, generally refers to conditions that are compatible to produce complexes between complementary binding members, i.e., between immobilized probes and complementary sample nucleic acids, but which does not result in any substantial complex formation between non-complementary nucleic acids (e.g., any complex formation which cannot be detected by normalizing against background signals to interfeature areas and/or control regions on the array).

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

Additional hybridization methods are described in references describing CGH techniques. (Kallionemi, et al. 1992 *Science* 258:818-821; WO 93/18186.) Several guides to general techniques are available. (See, e.g., Tijssen, Hybridization with Nucleic Acid Probes, Parts I and II, Elsevier, Amsterdam 1993.) For a description of techniques suitable for in situ hybridizations see, e.g., Gall et al. 1981 *Meth. Enzymol.* 21:470-480 and Angerer, et al. *Genetic Engineering: Principles and Methods*, Setlow and Hollaender, Eds. Vol 7, pgs 43-65 (Plenum Press, New York 1985); U.S. Pat. Nos. 6,335,167, 6,197,501, 5,830,645, and 5,665,549.

The term "primer", as used herein, refers to an oligonucleotide that has a nucleotide sequence that is complementary to a region of a target nucleic acid. A primer binds to the complementary region and is extended, using the target nucleic acid as the template, under primer extension conditions. A primer may be in the range of about 20 to about 60 nucleotides although primers outside of this length are envisioned. A "primer" can be extended from its 3' end by the action of a polymerase. An oligonucleotide that cannot be extended from its 3' end by the action of a polymerase is not a primer.

The term "primer extension conditions", as used herein, refers to conditions suitable for the extension of a primer that is bound to a complementary region in a target nucleic acid. Primer extension conditions include incubating a duplex nucleic acid with nucleotides, a polymerase and a buffer for a period of time at a certain temperature. Such conditions are well known in the art. The resulting new strand produced by primer extension is referred herein as a "primer extension product."

The term "amplifying", as used herein, refers to generating one or more copies of a target nucleic acid, using the target nucleic acid as a template.

The term "amplicon", as used herein, refers to the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences that contain a common region that is amplified, for example, a specific exon sequence present in a mixture of DNA fragments extracted from a sample. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complement's in a template polynucleotide that are required for the creation of reaction products. In one aspect, template-driven reactions are primer extensions with a nucleic acid polymerase or oligonucleotide ligations with a nucleic acid ligase. Such reactions include, for example, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR): Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. As used herein, the term "amplifying" means performing an amplification reaction.

The term "polymerase chain reaction" or "PCR", as used herein, refers to an enzymatic reaction in which a specific template DNA is amplified using one or more pairs of sequence specific primers. "PCR conditions" are the conditions in which PCR is performed, and include the presence of reagents (e.g., nucleotides, buffer, polymerase, etc) as well as temperature cycling (e.g., through cycles of temperatures suitable for denaturation, renaturation and extension), as is known in the art.

The term "complementary", as used herein, refers to a nucleotide sequence that base-pairs by non-covalent bonds to a target nucleic acid of interest. In the canonical Watson- Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is fully complementary to a target of interest such that every nucleotide in the sequence is complementary to every nucleotide in the target nucleic acid in the corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

The term "strand", as used herein, refers to a nucleic acid made up of nucleotides covalently linked together by phosphodiester bonds. One strand of nucleic acid does not include nucleotides that are associated solely through hydrogen bonding, i.e., via base-pairing, although that strand may be base-paired with a complementary strand via hydrogen bonding.

A nucleic acid may exist in a single stranded or a double-stranded form. A double stranded nucleic acid has two complementary strands of nucleic acid may be referred to herein as the "first" and "second" strands or some other arbitrary designation. The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.), as well as many pathogens, are known, and may be found in NCBI's Genbank database, for example. The second strand of a region is complementary to that region.

Certain embodiments of the invention include arrays, for example, a nucleic acid array. An "array," includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. By "immobilized" is meant that the moiety or moieties are stably associated with the substrate surface in the region, such that they do not separate from the region under conditions of using the array, e.g., hybridization and washing conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. Arrays of nucleic acids are known in the art, where representative arrays that may be modified to become arrays of the subject invention as described herein, include those described in: U.S. Pat. Nos. 6,656,740; 6,613,893; 6,599,693; 6,589,739; 6,587,579; 6,420,180; 6,387,636; 6,309,875; 6,232,072; 6,221,653; and 6,180,351 and the references cited therein.

The term "substrate", as used herein, refers to a surface upon which marker molecules or probes, e.g., an array, may be adhered. Glass slides are the most common substrate for biochips, although fused silica, silicon, plastic, and other materials are also suitable.

The substrate may be formed in essentially any shape. In one set of embodiments, the substrate has at least one surface that is substantially planar. However, in other embodiments, the substrate may also include indentations, protuberances, steps, ridges, terraces, or the like. The substrate may be formed from any suitable material, depending upon the application. For example, the substrate may be a silicon-based chip or a glass slide. Other suitable substrate materials for the arrays of the present invention include, for example, glasses, ceramics, plastics, metals, alloys, carbon, agarose, silica, quartz, cellulose, polyacrylamide, polyamide, polyimide, and gelatin, as well as other polymer supports or other solid-material supports. Polymers that may be used in the substrate include, for example, polystyrene, poly(tetra)fluoroethylene (PTFE), polyvinylidenedifluoride, polycarbonate, polymethylmethacrylate, polyvinylethylene, polyethyleneimine, polyoxymethylene (POM), polyvinylphenol, polylactides, polymethacrylimide (PMI), polyalkenesulfone (PAS), polypropylene, polyethylene, polyhydroxyethylmethacrylate (HEMA), polydimethylsiloxane, polyacrylamide, polyimide, various block co-polymers, etc.

The choice of nucleic acids to use as probes may be influenced by prior knowledge of the association of a particular chromosome or chromosomal region with certain disease conditions. (See, e.g., WO 93/18186 which provides a list of exemplary chromosomal abnormalities and associated diseases.) Alternatively, whole genome screening to identify new regions subject to frequent changes in copy number can be performed using the methods of the present invention discussed further below.

The term "dye," as used herein, generally refers to any organic or inorganic molecule or moiety that absorbs electromagnetic radiation, for example, at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule result in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

The invention provides novel, dendrimeric dye-containing oligonucleotide probes that are useful for high sensitivity FISH nucleic acids such as DNA and RNA. The oligonucleotide probes of the invention overcome a number of inadequacies and deficiencies of conventional fluorescent probes.

First, compared to existing fluorescent probes, there is no limitation to the number of fluorescent dyes that can be incorporated in the probes. Second, it is know that dendrimeric dyes are generally brighter than their individual counterparts leading to a more sensitive probe. Third, a unique feature of the fluorescent probes of the invention is the use of click chemistry generally leads to quantitative or near quantitative labeling. Furthermore, since the dye-containing moiety will be at the 5'- of the FISH probe, the fluorescent moieties do not affect hybridization of the probe with the target species such as genomic DNA or RNA.

In one aspect, the invention generally relates to an oligonucleotide probe. The oligonucleotide probe includes a nucleic acid sequence capable of hybridization with a target nucleic acid of interest; and a primer covalently attached to the oligonucleotide, wherein the primer is covalently attached to a dendrimeric group comprising two or more fluorescent moieties.

In certain preferred embodiments, the dendrimeric group is covalently attached to the primer at the 5'-end. (The FIGURE)

Fluorescent dyes useful in the fluorescent probes of the invention may be any suitable dyes, including cyanine dyes, rhodamine dyes, fluorone dyes, acridine dyes, oxazin dyes, phenanthridine dyes, for example. In certain preferred embodiments, the one or more fluorescent moieties are fluorescent dyes selected from Cy2, Cy3, Cy 3.5, Cy5, Cy5.5, Cy 7, IR dyes, Dyomics dyes, Oregon green 488, pacific blue, rhodamine green, and Alexa dyes.

The terms "dendrimer" or "dendrimeric", as used herein, refer to repeatedly branched molecules and molecules. Dendrimers are three dimensional, hyperbranched, monodisperse nanometric macromolecules obtained by a reiterative sequence of reactions. Dendrimers can be monovalent or multivalent. For example, multivalent dendrimers can be divalent, trivalent, tetravalent, pentavalent, hexavalent, heptavalent, octovalent, nanovalent or decavalent. In certain embodiments, the dendrimer may have, for example, 2-10 branches, 11-20 branches, or more than 20 branches. The dendrimer typically has a regularly repeated branching structure. When a dendritic structural unit extends from its preceding dendritic structural unit as an exact copy thereof, the extension of the unit is referred to as the subsequent "generation".

Dendrimers have been prepared via click chemistry, employing Diels-Alder reactions, thiol-yne reactions and azide-alkyne reactions, for example. (Franc, et al. 2009 *Chem. Eur. J. vol.* 15, Issue 23, pp. 5630-5639; Kato, et al. 2008 *J. Am. Chem. Soc.* 130 (15), pp. 5062-5064; Noda, et al. 1991 *Jpn. J. Psychiatry Neurol.* 45 (1): 107-8; Machaiah 1991 *Indian J. Exp. Biol.* 29 (5): 463-7; Franc, et al. 2008 *Chem. Comm. Pp.* 5267-5276.)

A number of dendrimer synthetic methodologies are known in the art. Synthetic methods of dendrimers include divergent methods wherein the dendrimer is assembled from a multifunctional core, which is extended outward by a series of reactions, for example, a Michael reaction.

Scheme 1

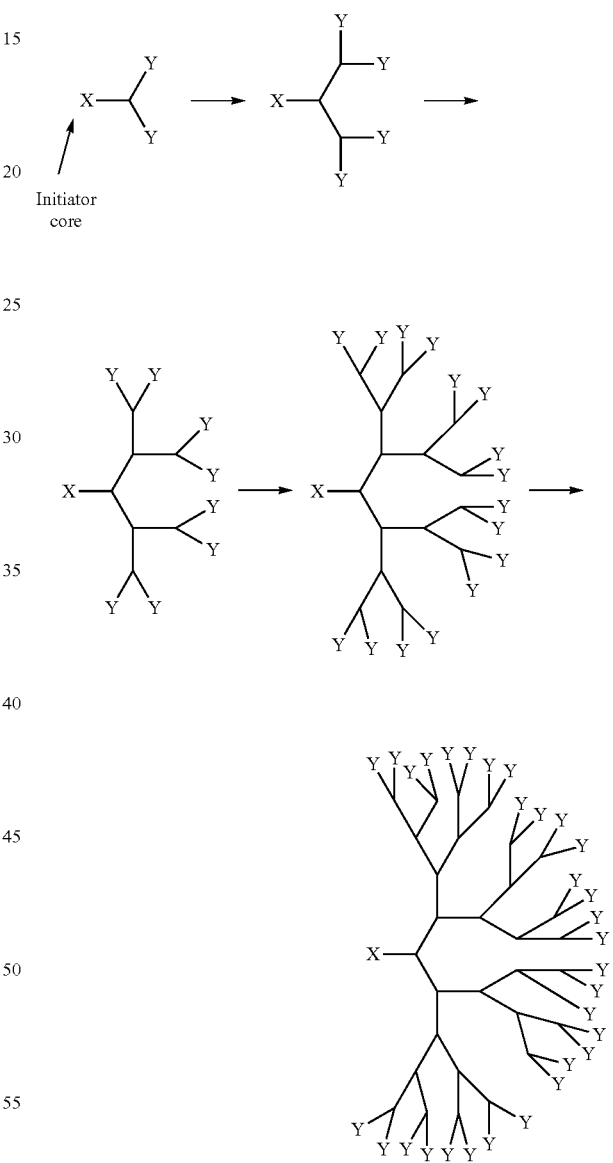

Syntheses methods of dendrimers also include convergent methods wherein the endrimers are built from small molecules that end up at the surface of the sphere, and reactions proceed inward building inward and are eventually attached to a core.

Scheme 2

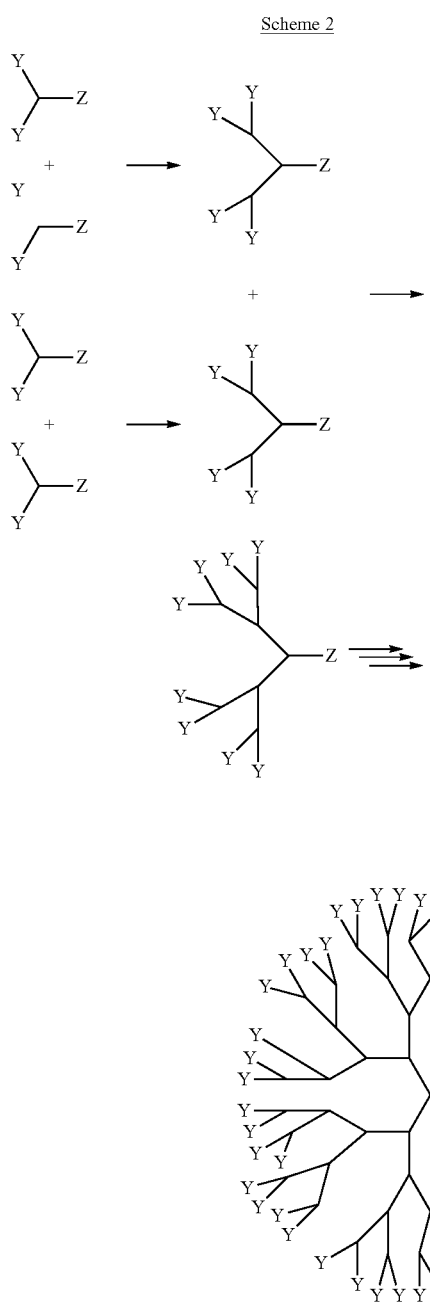

Each of the dendrimeric group may include any suitable generations of extensions, e.g., 2, 3, 4, 5, 6, 7, 8, 9, 10, more than 10.

Each of the dendrimeric group may include any suitable number of fluorescent moieties. In certain preferred embodiments, the dendrimeric group includes three or more fluorescent moieties (e.g., four or more, five or more, six or more, 10 or more).

In certain preferred embodiments, the dendrimeric group has the structural formula of

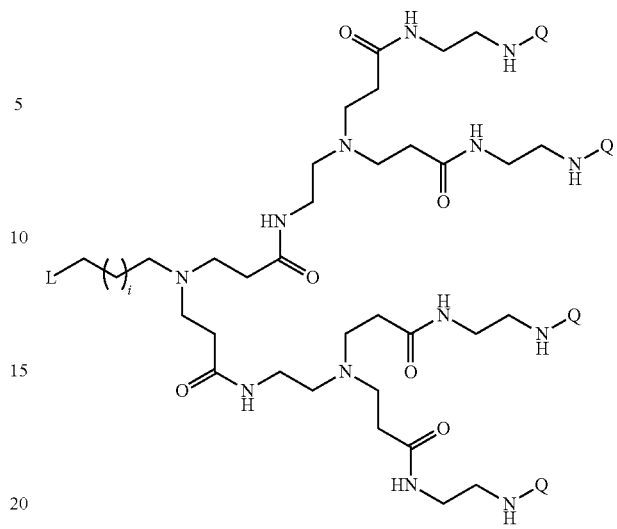

wherein L comprises a reactive group selected from alkynes, azides, thiol, -ene, isonitriles and tetrazines; i is an integer from about 0 to 6 (e.g., 1, 2, 3, 4, 5, 6); and Q is a fluorescent moiety selected from Cy2, Cy3, Cy 3.5, Cy5, Cy5.5, Cy 7, IR dyes, Dyomics dyes, Oregon green 488, pacific blue, rhodamine green, and Alexa dyes.

In certain preferred embodiments, the dendrimeric group is covalently linked to the primer. Any suitable reactions may be employed to couple the dendrimeric group is covalently linked to the primer. In certain preferred embodiments, the dendrimeric group is covalently coupled to the primer through a click chemistry reaction (or click reaction). As used herein, the term "click chemistry" refers to chemistry tailored to generate substances quickly and reliably by joining small modular units together (see, e.g., Kolb, et al. 2001 *Angewandte Chemie Intl. Ed.* 40:2004-2011; Evans 2007 *Australian J. Chem.* 60:384-395; Carlmark, et al. 2009 *Chem. Soc. Rev.* 38:352-362.

An exemplary click chemistry reaction is the azide-alkyne Huisgen cycloaddition (e.g., using a Copper (Cu) catalyst at room temperature). (Rostovtsev, et al. 2002 *Angew. Chemie Int'l Ed.* 41 (14): 2596-2599; Tornoe, et al. 2002 *J. Org. Chem.* 67 (9): 3057-3064.) Other examples of click chemistry include thiol-ene click reactions, Diels-Alder reaction and inverse electron demand Diels-Alder reaction, [4+1] cycloadditions between isonitriles (isocyanides) and tetrazines. (See, e.g., Hoyle, et al. 2010 *Angew. Chemie Int'l Ed.* 49 (9): 1540-1573; Blackman, et al. 2008 *J. Am. Chem. Soc.* 130 (41): 13518-13519; Devaraj, et al. 2008 *Bioconjugate Chem.* 19 (12): 2297-2299; Stöckmann, et al. 2011 *Org. Biomol. Chem.* 9, 7303-7305).

For example, the click reaction can be between an alkyne moiety present on the primer and an azide moiety present in the dendrimeric group. The click reaction can also be between an azide moiety present on the primer and an alkyne moiety present in the dendrimeric group.

In another aspect, the invention generally relates to a method for generating oligonucleotide probes. The method includes: generating a library of oligonucleotides; providing a plurality of primers each comprising an alkyne moiety; forming a library of amplicons wherein each amplicon comprises a member of the library of oligonucleotides and a primer from the plurality of primers; providing a dendrimeric group comprising two or more fluorescent moieties and comprises an azide moiety; and reacting the amplicons with the dendrimeric group by reacting the alkyne moiety with the azide moiety thereby generating a library of oligonucleotide probes.

In certain preferred embodiments, the dendrimeric group is covalently attached to each of the plurality of primers at the 5'-end. In certain preferred embodiments, the one or more fluorescent moieties are fluorescent dyes selected from Cy2, Cy3, Cy 3.5, Cy5, Cy5.5, Cy 7, IR dyes, Dyomics dyes, Oregon green 488, pacific blue, rhodamine green, and Alexa dyes. In certain preferred embodiments, the dendrimeric group has the structural formula of

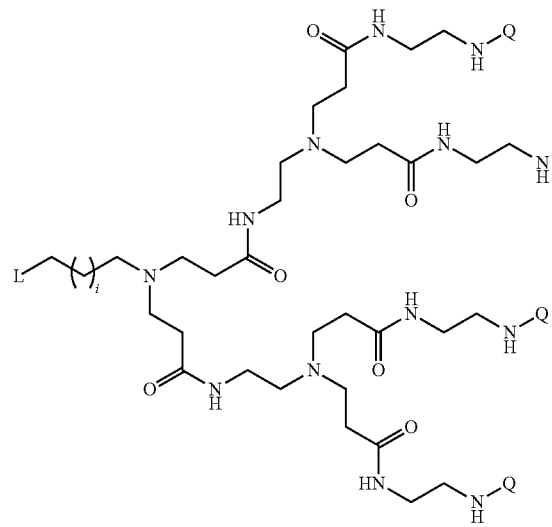

wherein L comprises a reactive group selected from alkynes, azides, thiol, -ene, isonitriles and tetrazines; i is an integer from about 0 to 6 (e.g., 1, 2, 3, 4, 5, 6); and Q is a fluorescent moiety selected from Cy2, Cy3, Cy 3.5, Cy5, Cy5.5, Cy 7, IR dyes, Dyomics dyes, Oregon green 488, pacific blue, rhodamine green, and Alexa dyes.

In yet another aspect, the invention generally relates to a method for detecting or analyzing a target nucleic acid of interest. The method includes: providing an oligonucleotide probe comprising a nucleic acid sequence capable of hybridization with a target nucleic acid of interest and a primer covalently attached a first reactive moiety; contacting the oligonucleotide probe with a sample to be analyzed for the presence of the target nucleic acid of interest under a condition such that, if the target nucleic acid of interest is present, a hybridization complex is formed between the oligonucleotide probe and the target nucleic acid of interest; and reacting the contacted sample with a dedrimeric imaging agent comprising two or more fluorescent moieties and a second reactive moiety, whereby the second reactive moiety reacts with the first reactive moiety to form a covalent bond; and imaging the two or more fluorescent moieties to detect or analyze the presence of the target nucleic acid of interest.

In certain preferred embodiments, the dendrimeric group is covalently attached to each of the plurality of primers at the 5'-end. In certain preferred embodiments, the one or more fluorescent moieties are fluorescent dyes selected from Cy2, Cy3, Cy 3.5, Cy5, Cy5.5, Cy 7, IR dyes, Dyomics dyes, Oregon green 488, pacific blue, rhodamine green, and Alexa dyes. In certain preferred embodiments, the dendrimeric group has the structural formula of

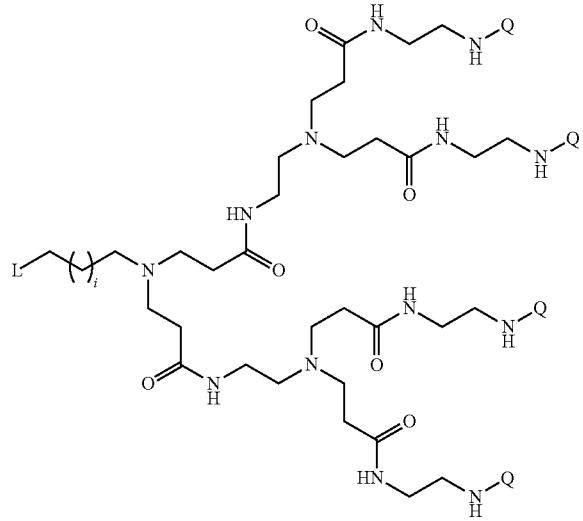

wherein L comprises a reactive group selected from alkynes, azides, thiol, -ene, isonitriles and tetrazines; i is an integer from about 0 to 6 (e.g., 1, 2, 3, 4, 5, 6); and Q is a fluorescent moiety selected from Cy2, Cy3, Cy 3.5, Cy5, Cy5.5, Cy 7, IR dyes, Dyomics dyes, Oregon green 488, pacific blue, rhodamine green, and Alexa dyes.

A suitable sample may comprise one or more targets, such as one or more of a protein; a peptide; a carbohydrate; a nucleic acid; a lipid; a small molecule; a toxin; a drug or drug-like molecule, or derivatives thereof; or may comprise a combination of targets that may be proteins; peptides; carbohydrates; nucleic acids; lipids; small molecules; toxins; drugs or drug-like molecules, or derivatives thereof. For example, a sample may comprise a defined combination of natural and/or chemically synthesized species. In certain embodiments, the composition of a sample may not be fully known.

The sample may include a cell, a group of cells, may be prepared from a cell or group of cells, may be a purified fraction from a cell preparation, may be a purified molecule. For example, the sample may comprise cells, such as mammalian cells (e.g., human cells); insect cells; yeast cells; fungal cells; and/or bacterial cells. The cells, for example, may be from multicellular organism (e.g., insects and mammals) derived from specific portions of the organism (e.g., specific tissues, organs, or fluids). Cells may be contacted by hybrids in vitro or in vivo, and may be contacted by hybrids when in suspension or when attached to a solid surface. Cells may not be significantly modified during the process, may be fixed to a solid support, and/or may be made permeable using standard methods.

The sample may include cells, products produced by cells, cellular components, and/or mixtures thereof. The sample may include cellular components, such as a nucleus, cytoplasm, plasma cell membrane, nucleolus, mitochondria, vacuoles, subcellular organelles, endoplasmic reticulum and/or Golgi apparatus. The sample may include cells, tissue samples, and/or organs, such as molecular antigens produced from groups of cells, tissue samples, and/or organs. In certain embodiments, the sample may comprise or be derived from, for example, clinical, industrial, agricultural and environmental samples. For example, sample material often may be of medical, veterinary, environmental, nutritional or industrial significance, and include body fluids, such as blood, serum, plasma, cerebrospinal fluid, synovial fluid, saliva, milk, sputum, lung aspirates, mucus, teardrops, exudates, secretions, urine, and fecal matter; microbial culture fluids; aerosols; crop materials; animal meat (e.g., for human consumption or animal feed); and soils and ground waters.

In certain embodiments, the sample may include molecules in pathogens, viruses, bacteria, yeast, fungi, amoebae and insects; molecules in diseased or non-diseased pest animals such as mice and rats; molecules in diseased and non-diseased domestic animals, such as domestic equines, bovines, porcines, caprines, canines, felines, avians and fish; and molecules in diseased and non-diseased humans.

In certain embodiments, the sample may include biological samples derived from a human or other animal source (e.g., body fluids, such as blood, serum, plasma, cerebrospinal fluid, synovial fluid, saliva, milk, sputum, lung aspirates, mucus, teardrops, exudates, secretions, urine, a biopsy sample, a histology tissue sample, a PAP smear, a mole, a wart, etc.) including samples derived from a bacterial or viral preparation, as well as other samples (e.g., agricultural products, waste or drinking water, milk or other processed foodstuff, air, etc.). In certain embodiments, the sample may comprise one or more of the following: tissue cells, cells cultured in vitro, recombinant cells, infected cells, cells from laboratory animals, cells from mammal patients, cells from human patients, mesenchemal stem cells, stem cells, immuno-competent cells, adipose cells, fibroblasts, natural-killer cells (NK-cells), monocytes, lymphocytes, lymph node cells, T-cells, B-cells, exudate cells, effusion cells, cancer cells, blood cells, red blood cells, leukocytes, white blood cells, organ cells, skin cells, liver cells, splenocytes, kidney cells, intestinal cells, lung cells, heart cells, or neuronal cells.

An exemplary embodiment of the invention is provided in Scheme 3.

Scheme 3

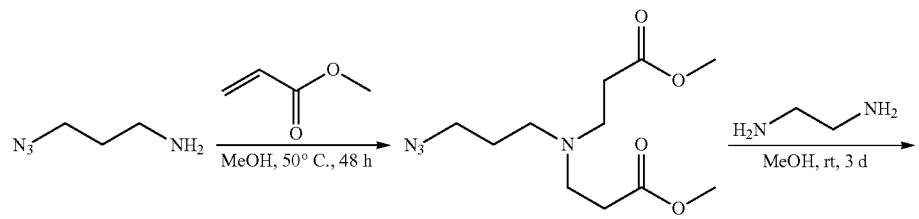

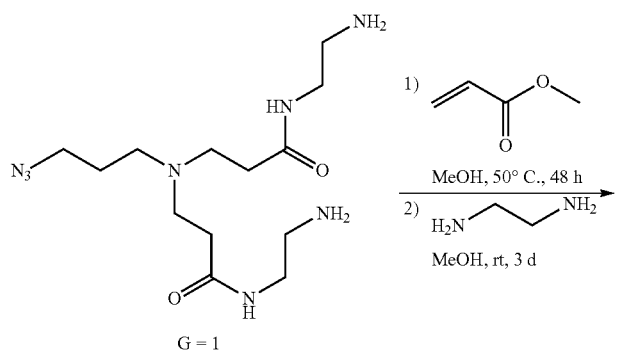

G = 1

-continued
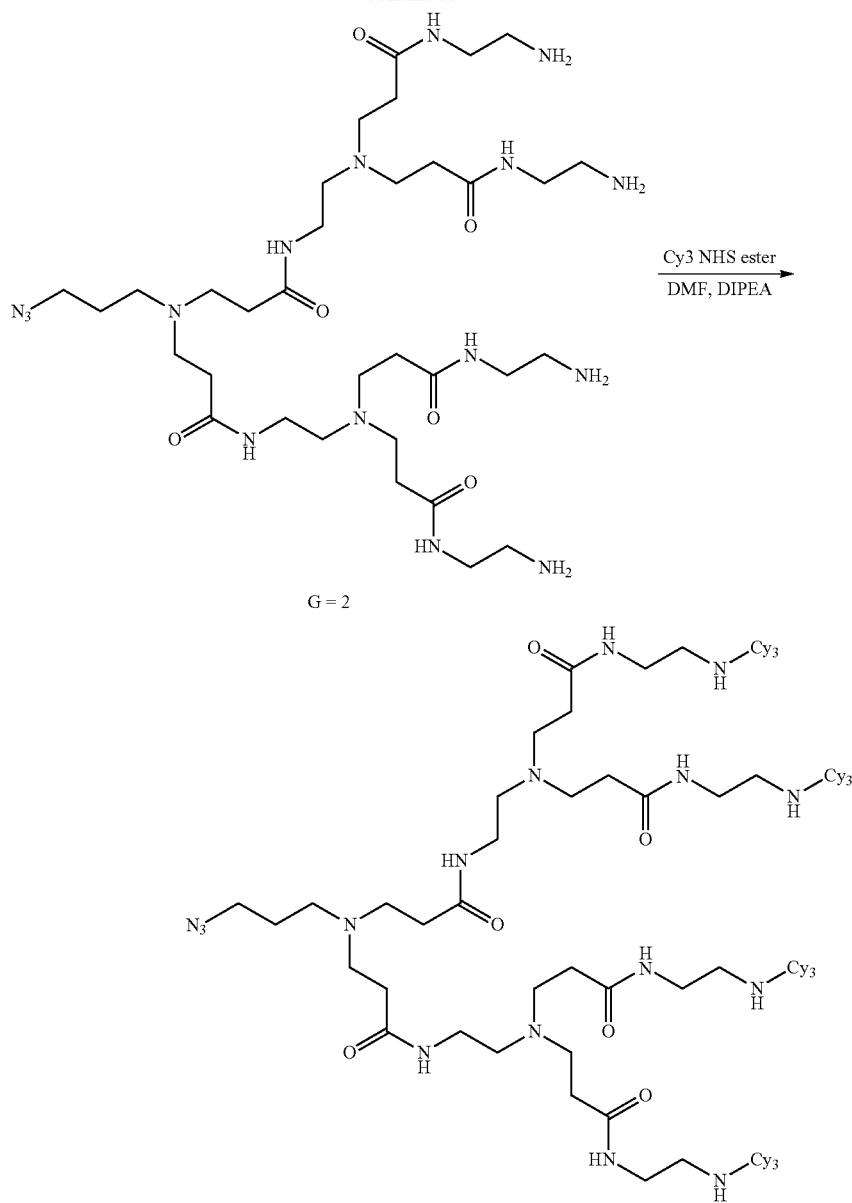
G = 2
Cy3 NHS ester
DMF, DIPEA
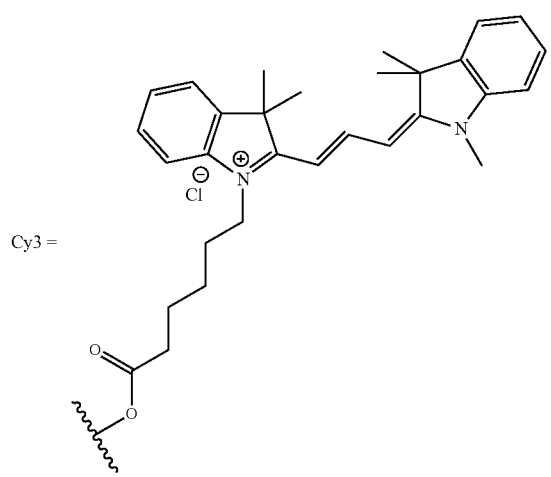 [SMILES: *OC(=O)CCCCC[N+]1=C(/C=C/C=C2/N(C)c3ccccc3C2(C)C)C(C)(C)c2ccccc21 ; [Cl-]]
Cy3 =

Scheme 4

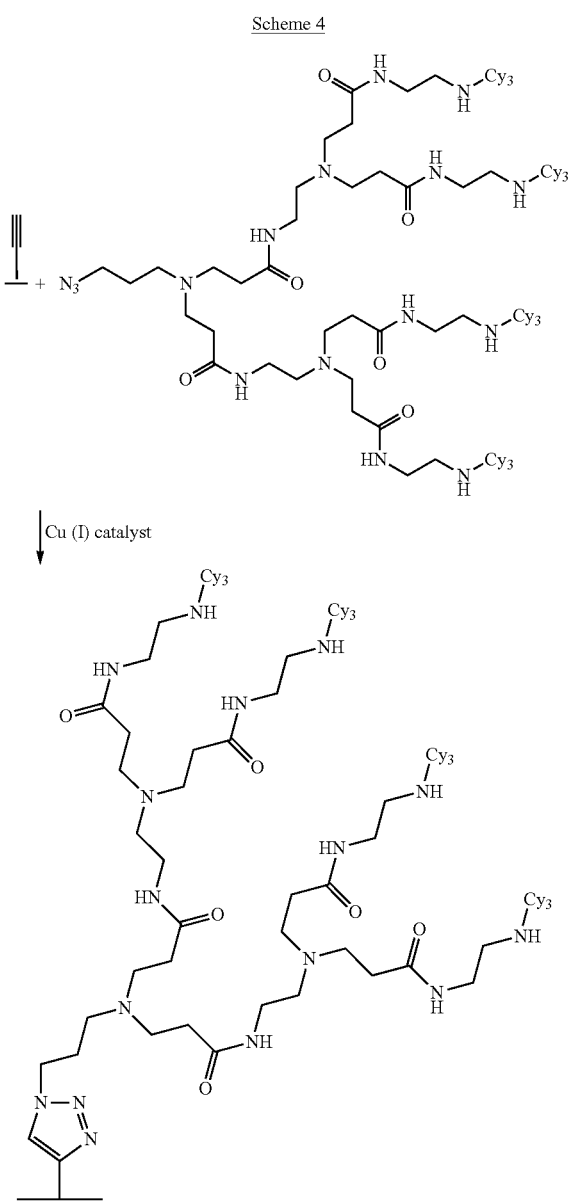

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. An oligonucleotide probe, comprising:
   (a) a nucleic acid sequence capable of hybridization with genomic DNA or a cellular RNA from a cell of interest;
   (b) a primer sequence that is covalently attached to the 5' end of the nucleic acid sequence of (a); and
   (c) a dendrimeric group that is covalently attached to the primer sequence of (b) and comprises two or more fluorescent moieties.

2. The oligonucleotide probe of claim 1, wherein the dendrimeric group is covalently attached to the 5' end of the primer sequence.

3. The oligonucleotide probe of claim 1, wherein the one or more fluorescent moieties are fluorescent dyes selected from Cy2, Cy3, Cy 3.5, Cy5, Cy5.5, Cy 7, IR dyes, Dyomics dyes, Oregon green 488, pacific blue, rhodamine green, and Alexa dyes.

4. The oligonucleotide probe of claim 1, wherein the dendrimeric group comprising three or more fluorescent moieties.

5. The oligonucleotide probe of claim 1, wherein the dendrimeric group has the structural formula of

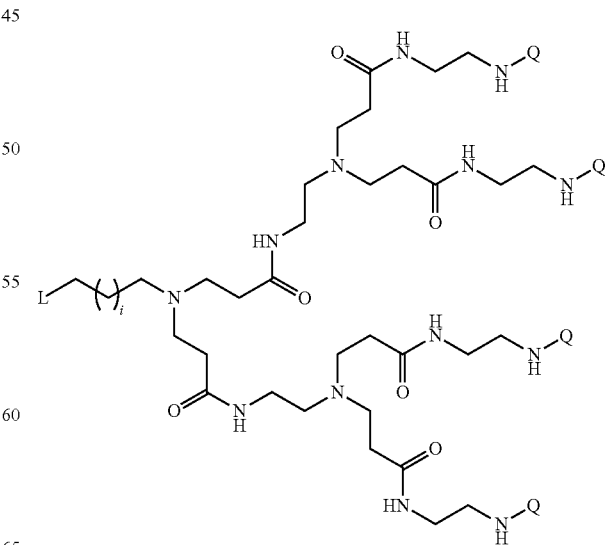

wherein
- L comprises a reactive group selected from alkynes, azides, thiol, -ene, isonitriles and tetrazines;
- i is an integer from about 0 to 6; and
- Q is a fluorescent moiety selected from Cy2, Cy3, Cy 3.5, Cy5, Cy5.5, Cy 7, IR dyes, Dyomics dyes, Oregon green 488, pacific blue, rhodamine green, and Alexa dyes.

6. The oligonucleotide probe of claim 1, wherein the dendrimeric group is covalently linked to the primer through a click reaction.

7. The oligonucleotide probe of claim 6, wherein the click reaction is between an alkyne moiety present on the primer and an azide moiety present in the dendrimeric group.

8. The oligonucleotide probe of claim 6, wherein the click reaction is between an azide moiety present on the primer and an alkyne moiety present in the dendrimeric group.

* * * * *